US008016841B2

(12) United States Patent
Magnusson et al.

(10) Patent No.: US 8,016,841 B2
(45) Date of Patent: Sep. 13, 2011

(54) MESH IMPLANT WITH AN INTERLOCKING KNITTED STRUCTURE

(75) Inventors: Henrik Magnusson, Uppsala (SE); Torbjörn Mathisen, Älvsjö (SE)

(73) Assignee: Novus Scientific Pte. Ltd., Singapore (SG)

( * ) Notice: Subject to any disclaimer, the term of this patent is extended or adjusted under 35 U.S.C. 154(b) by 985 days.

(21) Appl. No.: 11/808,563

(22) Filed: Jun. 11, 2007

(65) Prior Publication Data

US 2008/0306494 A1 Dec. 11, 2008

(51) Int. Cl.
*A61B 17/08* (2006.01)
(52) U.S. Cl. .................... 606/151; 623/23.72
(58) Field of Classification Search .............. 623/23.72, 623/23.75; 606/151, 154, 213, 200, 228
See application file for complete search history.

(56) References Cited

U.S. PATENT DOCUMENTS

| | | | |
|---|---|---|---|
| 5,686,090 A | 11/1997 | Schilder et al. | |
| 5,733,337 A | 3/1998 | Carr et al. | |
| 6,162,962 A | 12/2000 | Hinsch et al. | |
| 6,268,544 B1 * | 7/2001 | Court et al. | 602/41 |
| 6,319,264 B1 | 11/2001 | Törmälä et al. | |
| 6,514,515 B1 | 2/2003 | Williams | |
| 7,749,273 B2 * | 7/2010 | Cauthen et al. | 623/17.11 |
| 2002/0042128 A1 | 4/2002 | Bowlin et al. | |
| 2002/0062152 A1 | 5/2002 | Dauner et al. | |
| 2003/0082148 A1 | 5/2003 | Ludwig et al. | |
| 2003/0193104 A1 | 10/2003 | Melican et al. | |
| 2004/0138762 A1 * | 7/2004 | Therin et al. | 623/23.75 |
| 2005/0070930 A1 * | 3/2005 | Kammerer | 606/151 |
| 2005/0113849 A1 | 5/2005 | Popadiuk et al. | |
| 2005/0267325 A1 * | 12/2005 | Bouchier et al. | 600/37 |
| 2006/0083767 A1 | 4/2006 | Deusch et al. | |
| 2006/0142786 A1 | 6/2006 | Mathisen et al. | |
| 2007/0142698 A1 * | 6/2007 | Bourne et al. | 600/30 |
| 2007/0299542 A1 | 12/2007 | Mathisen et al. | |

FOREIGN PATENT DOCUMENTS

| | | |
|---|---|---|
| EP | 1 252 905 A2 | 10/2002 |
| EP | 0 797 962 B1 | 5/2004 |
| EP | 1 674 048 A1 | 6/2006 |
| WO | WO-2004/050133 A2 | 6/2004 |

OTHER PUBLICATIONS

"Standard Test Method for Bursting Strength of Textiles—Constant-Rate-of-Traverse (CRT) Ball Burst Test," ASTM—International, Designation: D 3787-01.

(Continued)

*Primary Examiner* — Darwin Erezo
*Assistant Examiner* — Alexander Orkin
(74) *Attorney, Agent, or Firm* — Foley & Lardner LLP

(57) ABSTRACT

A resorbable polymeric mesh implant is provided for use in the reconstruction of soft tissue defects. The mesh implant is provided with an interlocking knitted structure comprising two or more sets of fibers with different times of degradation, allowing a stepwise increase in the relative distension of the overall mesh over time. The filamentous fibers are knitted together, wherein the filaments of the first set of fibers are interlaced into the filaments of the second set of fibers and at least partly traverse the knit pattern of the second set of fibers such that the filaments of the first set of fibers lock the movement of the part of the mesh formed by the second set of fibers.

18 Claims, 2 Drawing Sheets

OTHER PUBLICATIONS

D. Roylance, "Introduction to Composite Materials," Mar. 24, 2000, pp. 1-7, Dept. of Materials Science and Engineering, MIT, Cambridge, MA.

K. Van de Velde et al., "Biopolymers: overview of several properties and consequences on their applications," Sep. 11, 2001, pp. 433-442, Polymer Testing 21, Elsevier Science Ltd., Zwijnaarde, Belgium.

T. Mathisen et al., US PTO Office Action, U.S. Appl. No. 11/019,534, dated Feb. 11, 2008, 10 pgs.

T. Mathisen et al., US PTO Office Action, U.S. Appl. No. 11/019,534, dated Jun. 20, 2007, 12 pgs.

T. Mathisen et al., US PTO Office Action, U.S. Appl. No. 11/019,534, dated Jun. 20, 2007, 12 pgs.

T. Mathisen et al., US PTO Office Action, U.S. Appl. No. 11/019,534, dated Aug. 28, 2008, 10 pgs.

T. Mathisen et al., US PTO Office Action, U.S. Appl. No. 11/019,534, dated Nov. 16, 2006, 12 pgs.

T. Mathisen et al., US PTO Office Action, U.S. Appl. No. 11/472,563, dated Nov. 12, 2008, 14 pgs.

U. Klinge et al., "Abnormal Collagen I to III Distribution in the Skin of Patients with Incisional Hernia", European Surgical Research, 2000, pp. 43-48.

W. H. de Jong et al., "Late tissue reactions and degradation of biodegradable polylactide implants. An experimental study in rats," National Institute of Public Health and the Environment (Bilthoven, The Netherlands), Report No. 605148 006, Jun. 1996, pp. 1-38.

K. Junge et al., "Elasticity of the anterior abdominal wall and impact for reparation of incisional hernias using mesh implants," Hernia, vol. 5, No. 3, Sep. 14, 2001, pp. 113-118.

T. Mathisen et al., US PTO Final Office Action, U.S. Appl. No. 11/472,563, dated Jun. 25, 2009, 12 pgs.

T. Mathisen et al., U.S. PTO Final Office Action, U.S. Appl. No. 11/472,563, dated Dec. 23, 2009, 12 pgs.

Mathisen et al., U.S. PTO Office Action, U.S. Appl. No. 11/472,563, dated Oct. 28, 2009, 13 pgs.

T. Mathisen et al., US PTO Final Office Action, U.S. Appl. No. 11/019,534, dated Aug. 27, 2009, 11 pgs.

T. Mathisen et al., U.S. PTO Final Office Action, U.S. Appl. No. 11/019,534, dated Aug. 5, 2010, 14 pgs.

U.S. Appl. No. 12/952,723, filed Nov. 23, 2010, Magnusson et al.

U.S. Appl. No. 13/004,530, filed Jan. 11, 2011, Mathisen et al.

\* cited by examiner

MESH IMPLANT WITH AN INTERLOCKING KNITTED STRUCTURE

FIELD OF THE INVENTION

The present invention relates to a resorbable polymeric mesh implant with an interlocking knitted structure comprising two or more sets of fibers with different times of degradation, allowing a stepwise increase in the relative distension of the overall mesh over time, intended to be used in the reconstruction of soft tissue defects.

BACKGROUND OF THE INVENTION

A hernia is an abnormal protrusion of a peritoneal-lined sac through the musculo-aponeurotic covering of the abdomen, the most common site for a hernia being the groin. Types of hernias are, among others, inguinal hernia or femoral hernia, hiatal hernia, umbilical hernia and incisional hernia, the latter being a hernia that pushes through a past surgical incision or operation site.

Hernias are repaired by a surgical procedure where the protrusion is retracted to its original position within the abdominal cavity, and subsequent healing is facilitated by covering the abdominal wall defect with a surgical implant. This can be done under local or general anesthesia using a laparoscope or an open incision technique.

Within the field of surgical repair of soft tissue defects such as hernias, use is often made of a mesh implant fabricated of a non-resorbable material that is inserted to cover the area of the tissue defect without sewing together the surrounding muscles. The mesh implant is used in order to support the regenerating tissue and works by mechanical closure of the defect as well as by inducing a strong scar fibrous tissue around the mesh implant. Such a mesh implant is most often made of various plastics, which are known to stay biostable and safe for a number of years after implantation. However, measurements of nine common mesh materials show a lower elasticity (with a mean value of approximately 15%) than that of the intact abdominal wall (23-32%) (K. Junge et al.: Elasticity of the anterior abdominal wall and impact for reparation of incisional hernias using mesh implants. *Hernia* 2001, no. 5, p. 113-118), which could result in discomfort, inflammation and recurrence of the hernia. Furthermore, permanently introducing a foreign material into the human or animal body could be accompanied with side effects such as migration, chronic inflammation, risk of infection, etc. The introduction of a relatively large inert implant is also likely to induce a long-term foreign body-reaction caused by the body's immune defense system. As a result, the mesh implant may crumple up and lose its tissue supporting function.

A solution to this is described in U.S. Pat. No. 6,319,264 which describes a porous, flexible and fibrous hernia mesh comprising two functional layers, wherein the first layer is a rapidly degradable polymer layer facing the fascia, and wherein the second layer is a more slowly degradable polymer layer. The mesh described in U.S. Pat. No. 6,319,264 acts as a temporary support until connective scar tissue has strengthened enough and can replace the mesh, when the second layer finally degrades. However, U.S. Pat. No. 6,319,264 is silent as to the load situation found over the tissue defect area and to any related adjustment of the relative distension of the hernia mesh.

Patent application EP 0797962 describes a mesh implant with a basic structure made from a knitted fabric comprising non-resorbable material or resorbable material, wherein the mesh is designed to stretch to allow movement in the underlying tissue. To ease the procedure of cutting and handling the mesh prior to insertion, the basic structure can be strengthened by adding a stiffener. The stiffener comprises a resorbable material which is either coated onto the knitted fibers or supplied as fibers which are woven together with (i.e. in the same pattern as) the fibers of the basic structure. This stiffening material is designed to resorb soon after surgery. However, the mesh implant provided in patent application EP 0797962 offers no particular measures to facilitate the primary formation of fibrotic tissue during the early stages of wound healing.

The U.S. Patent Application No. 2006/0142786, which is assigned to the present assignee, describes a mesh implant of a resorbable polymer comprising at least two materials, wherein the second material is substantially degraded at a later point in time than the first material following the time of implantation. The mesh implant is adapted to have a predetermined modulus of elasticity that gradually is decreased until the implant is completely degraded and subsequently absorbed. Due to the gradual decrease in the modulus of elasticity of the inventive mesh implant, the regenerating tissue may progressively take over the load applied to the tissue defect area. The U.S. Patent Application No. 2006/0142786 describes using materials with different elasticity overlaid on each other to achieve a gradual change in overall elasticity of the implant. To tailor for the properties of a mesh by choosing different materials may, however, in the case of a resorbable mesh be difficult, since the selection of suitable material commercially available is limited. In addition, these materials may be expensive and/or difficult to handle during the manufacturing of the mesh. The entire contents of U.S. Patent Application No. 2006/0142786 is incorporated herein by reference for the devices, techniques, and methods disclosed therein.

Consequently, there is still a need for an improved mesh implant which facilitates the healing process by relieving the tissue during initial stages of healing and allows the regenerating tissue to gradually take over the load during the progression of healing. It is therefore an object of the present invention to provide such a mesh implant which is completely degradable.

SUMMARY OF THE INVENTION

The present invention provides a mesh implant with characteristics allowing it to initially promote proper healing of the tissue lesion and thereafter gradually adjust to match conditions of the underlying tissue structures of the human body, such as the abdominal wall. This is achieved in a first embodiment by constructing a mesh with two different co-knitted materials with different degradation times relative to the time of implantation.

The mesh implant comprises at least a first type of fibers and a second type of fibers knitted together in an interlocking manner, wherein the second type of fibers is substantially degraded at a later point in time than the first type of fibers, following the time of implantation of the mesh implant. The mesh implant is adapted to have a substantially constant low relative distension during the primary wound healing period, after which period the relative distension is incrementally increased until the mesh implant substantially loses its mechanical properties and subsequently is completely degraded and absorbed by the body. These changes in the relative distension of the mesh are achieved by using filamentous fibers that are knitted together such that the filaments of the first set of fibers restrict the movement of the part of the mesh formed by the second set of fibers. When the first set of fibers is degraded, the relative distension of the mesh implant is substantially increased due to the fact that the movement of the part of the mesh formed by the second set of fibers is no longer constrained by the first set of fibers. During the initial stages of healing, the mesh restricts the movement of the underlying tissue in order to facilitate the primary steps in tissue regeneration. In addition, the porous structure of the knitted mesh promotes the ingrowth of new tissue. The regenerating tissue may thereafter gradually take over the load applied to the tissue defect area, as a result of the gradual increase in flexibility of the inventive mesh implant, until the mesh implant is completely absorbed. With the inventive mesh implant there is no longer a need for inert, non-resorbable, long-term supporting structures and the risk of postoperative rupture or discomfort due to incompatible elasticity of the mesh is minimized. In addition, the present invention can utilize known resorbable material or materials.

DETAILED DESCRIPTION OF PREFERRED EMBODIMENTS

The present invention is intended to be used in repair of soft tissue, i.e. tissue having some form of mobility and flexibility, including but not limited to the abdominal wall, inner organs, aponeurotic structures, muscles, tendons, ligaments, but excluding e.g. bones and cartilage.

The present invention is based on the current knowledge that primary wound healing usually occurs over a time period of 2 to 14 days, followed by a remodeling period, which may extend up to and over 6 months. The primary stage of wound healing is characterized by collagen deposition, granulation tissue formation and angiogenesis. During this stage, it is desirable to minimize the movement within the wound area. Thereafter, during the remodeling period, the newly formed tissue will undergo several phases, during which the tissue gradually becomes more specific to support the various stress situations found in the area. The inventors of the present invention therefore suggest that a device used to temporarily support the tissue defect in the area where the tissue is exposed to various stress situations should be so designed as to allow the newly formed tissue to gradually take over the load during the remodeling phase and thus build up the strength and compliance needed to take over the full load once the support from the temporarily implanted device is lost.

Furthermore, gradually changing elasticity of the mesh implant should be achieved by using two or more filamentous materials, wherein the filamentous fibers are knitted together. In addition, the filaments of a first set of fibers are interlaced into the filaments of a second set of fibers such that the filaments of the first set of fibers restrict the movement of the mesh formed by the second set of fibers.

Figure 1:
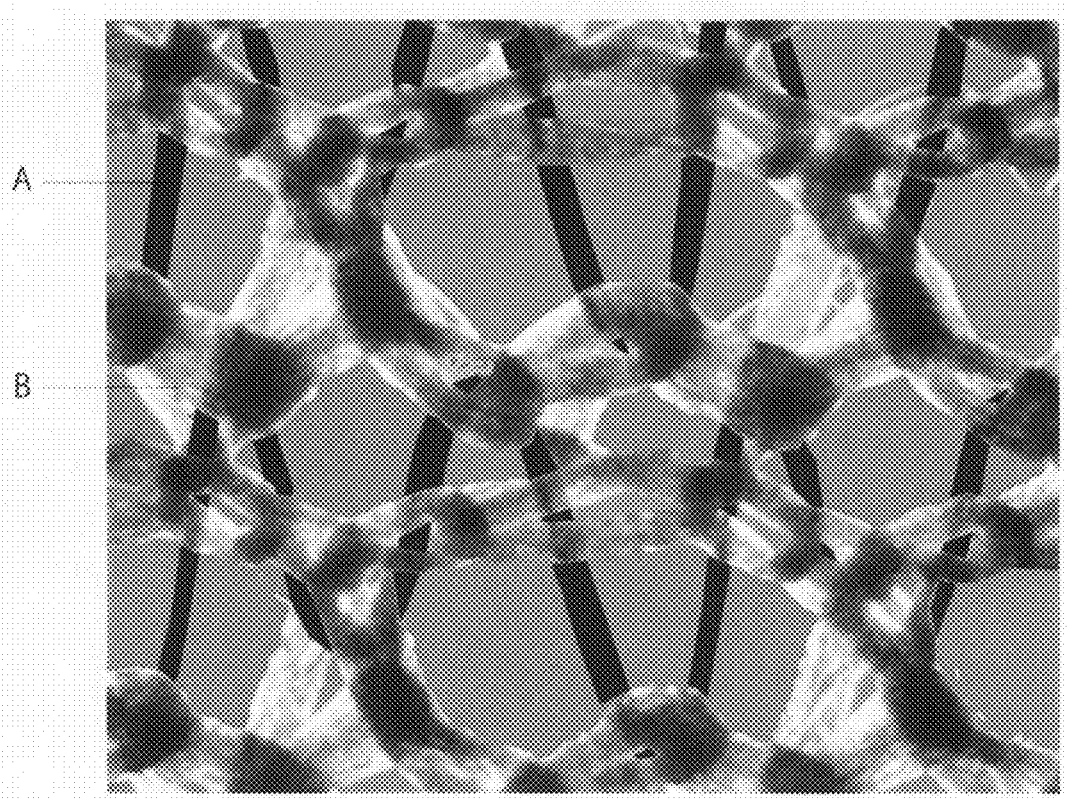
FIG. 1 shows a first embodiment of the present invention, wherein the mesh implant is comprised of two co-knitted sets of fibers A and B.

FIG. 1 schematically shows a first embodiment of the present invention, wherein the mesh implant comprises two resorbable filamentous sets of fibers, fibers A and fibers B. Fibers A are characterized by a time of substantial degradation, $t_A$. Consequently, fibers B are characterized by a time of substantial degradation, $t_B$. Fibers B are substantially degraded at a later point in time than fibers A, following the time of implantation of the mesh implant, i.e. $t_A < t_B$. The time of substantial degradation is herein defined as the point in time at which the material substantially loses its original integrity.

For the first embodiment of the present invention, $t_A$ is in the time range of 2 to 40 days, more preferably 5 to 30 days, or even more preferably 10 to 20 days after the time of implantation, i.e. $t=t_0$, and $t_B$ is at least 3-18 months after the time of implantation, preferably in the time range of 6-12 months.

To achieve the gradual adjustment from promoting initial healing to conditions matching the underlying tissue structures of the wound site, an interlocking knit of the different fibers of the mesh implant is used, wherein the different fibers have different times of resorption relative to the time of implantation. The interlocking knit patterns can be such that the first set of fibers at least partly traverses the pores formed by the second set of fibers (see FIG. 1) or even physically brings together (or close to one another) two or more points on the threads of the second set of fibers, thereby restricting the overall size of the pores in the mesh implant. The degradation of the first set of fibers allows increased pore size of the overall mesh, and thereby promotes further accumulation of extracellular matrix, fibroblasts, and other cells necessary for regeneration of the tissue. As mentioned, the increase in pore size is due to an expansion or opening up of the knit pattern after degradation of the first set of fibers.

An elastic material is by definition a material that can stretch to a certain extent in response to a pulling or pushing force in at least one direction and thereafter return to substantially its original shape and size when released. Since the direction in which said force is applied can vary infinitely, elasticity of a material is a complex function. On the other hand, relative distension of a material, measured using a ball burst testing apparatus, is a definable characteristic. Here, the material is subjected to a steel ball exerting a pushing force perpendicular to the plane of the flat material and the maximum length the ball can travel without failure of the material is used to calculate relative distension. However, the term distension does not encompass the ability of a material to return to its original size and shape.

As mentioned, the overall support characteristics of the mesh implant can be measured as relative distension of the mesh using a ball burst testing apparatus. The relative distension of a mesh, and in particular the changes in the relative distension of the mesh according to the present invention over time after implantation into the body, is governed by two main factors, either separately or in combination. The first factor, which has been touched upon above, is the change in relative distension after degradation of one set of fibers resulting from the distortion or change of the overall mesh pattern itself, i.e. a change in relative distension which can occur even with fibers comprising completely inelastic materials. To illustrate, even a mesh made of inelastic material, such as a common fishing net, exhibits relative distension when subjected to a force by increasing the pore diameter in one dimension while decreasing the pore diameter in another dimension, i.e. distorting the shape of the pores. Therefore, since the first set of fibers initially lock the pattern of the second set of fibers in the present mesh; degradation will lead to liberation of the mesh formed by the second set of fibers alone which can result in a higher overall relative distension of the mesh implant. The second factor affecting relative distension is the differences in inherent elasticity of the fiber materials themselves, depending on the composition of the materials used. In particular, the material of the first set of fibers can be less elastic than the material in the second set of fibers, such that after degradation of the first material the overall elasticity of the mesh is increased due to loss of the less elastic first material. Therefore, the relative distension can be varied by using different materials and/or different knit patterns, which provides a wide range of possible scenarios for the change in relative distension of the mesh implant over time.

Figure 2:
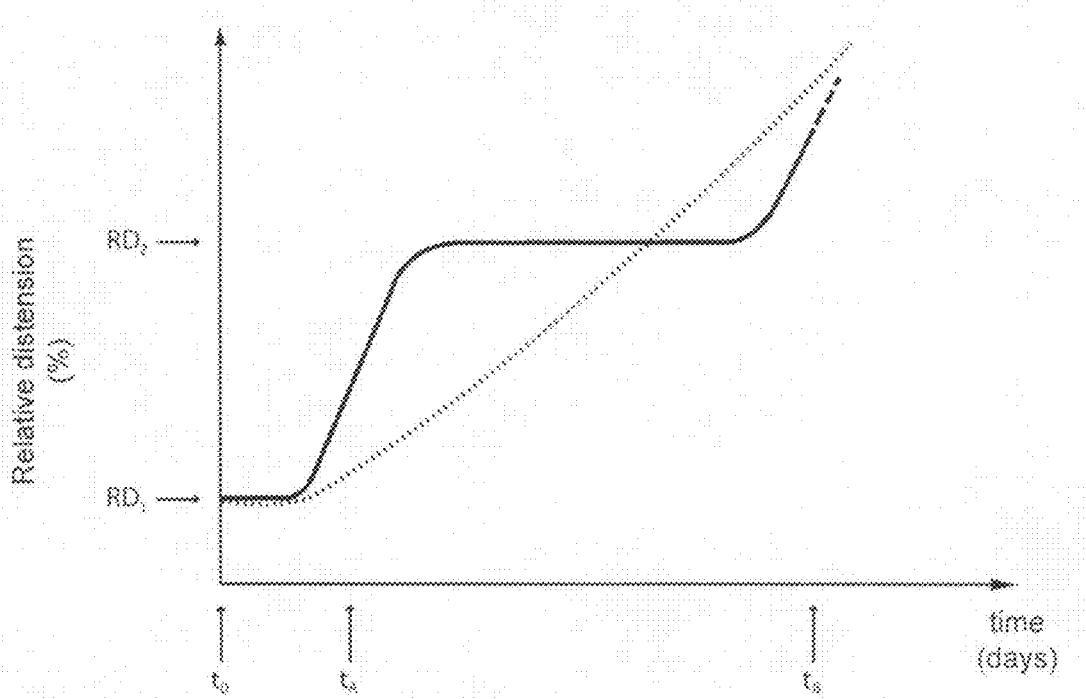
FIG. 2 shows the relative distension of the mesh implant shown in FIG. 1 as a function of time (not to scale).

FIG. 2 shows a schematic of the relative distension, RD, of the mesh implant shown in FIG. 1 as a function of time, t. Initially, until $t=t_A$, i.e. the time of substantial degradation for fibers A, the relative distension, $RD_1$, is essentially constant and preferably low, 0-10%, more preferably 3-7%. The relative distension in this phase is a result of the interlocking knitted structure of the two sets of fibers, as has been discussed above. At $t=t_A$, the relative distension of the mesh implant changes to a new, higher relative distension, $RD_2$, which is essentially solely dependent on the knit pattern and material of fibers B. Preferably, $RD_2$ is above 10%, more preferably 15-25%. Thus, $RD_2$ corresponds to a relative distension of the mesh implant that approaches the elasticity of the surrounding tissue, so that the flexibility of said tissue is not substantially restricted, at least not for minor movement.

Figure 3:
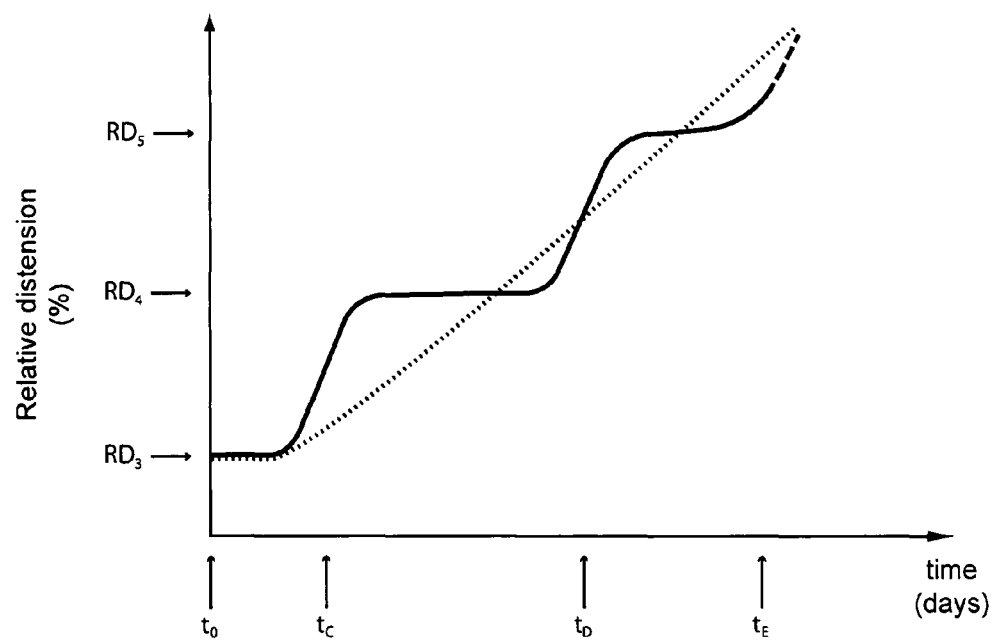
FIG. 3 shows the relative distension of a second embodiment of the present invention, wherein the mesh implant is comprised of three co-knitted sets of fibers, C, D and E, as a function of time (not to scale).

In a second embodiment of the inventive mesh implant a mesh implant comprises three sets of fibers, C, D and E, each characterized by a specific time of degradation, such that $t_C<t_D<t_E$. FIG. 3 shows the relative distension, RD, of such a mesh implant as a function of time, t. In this embodiment, $RD_3$ is understood to be a function of the interlocking knitted structure of the three sets of fibers, $RD_4$ a function of the interlocking knitted structure of fibers D and E, and, consequently, $RD_5$ a function of the mesh structure solely formed by fibers E. Furthermore, $RD_3<RD_4<RD_5$, conferring a gradual increase in the overall elasticity of the mesh implant. Thus, in the alternative embodiment, the mesh implant comprises three sets of fibers C, D and E. This embodiment approximates more closely the ideal increase in RD (for many different types of tissues) of such a mesh implant, illustrated as a dotted line in FIGS. 2 and 3.

In the second embodiment, $t_C$ is, comparable to $t_A$ in the first embodiment, in the time range of 2 to 40 days, more preferably 5 to 30 days, or even more preferably 10 to 20 days after the time of implantation, with the intention that $t_C$ is equivalent to the time of initial healing. Time $t_E$ is at least 3-18 months after the time of implantation, preferably in the time range of 6-12 months. Time $t_D$ can thus be anywhere between 2 days and 18 months, as long as $t_C<t_D<t_E$.

Corresponding to the values of $RD_1$ and $RD_2$ in the first embodiment, $RD_3$, $RD_4$ and $RD_5$ should be evenly spread over the range of from 0% to 25-30%, where the latter value corresponds to the relative distension of the abdominal wall. $RD_3$ is preferably in the range of 0-10% or more preferably 3-7%. $RD_5$ is preferably above 20%, more preferably in the range of 23-28%. $RD_4$ can thus be anywhere between 0% and approximately 30%, as long as $RD_3<RD_4<RD_5$.

In other embodiments, the mesh implant according to the present invention can comprise four or five sets of fibers, taking into consideration the fact that each successive set of fibers increases the mesh implant's approximation to the ideal increase in relative distension of such a mesh implant, illustrated as a dotted line in FIGS. 2 and 3.

It should be noted that the ability of a material to stretch in a particular embodiment need not have the same value in all directions, thus the ability of a material to stretch in for instance one direction along the plane of the mesh implant need not be identical to the ability of a material to stretch in the perpendicular planar direction. Consequently, two embodiments can have the same relative distension (measured at an angle perpendicular to the plane of the mesh implant), but exhibit different abilities to stretch in different directions in the plane of the mesh implant.

In the embodiments described above, the mesh implant can be fixed after implantation with for instance suitable sutures, staples, fixation, pins, adhesives or the like. In some applications of the implant, the pressure from the surrounding tissue may be enough for initial fixation until newly regenerating tissue anchors the implant by tissue through growth.

During the described time of resorption for the overall mesh implant the load applied to the mesh will gradually be taken over by the surrounding and ingrowing tissue, due to the step-wise degradation of the different sets of fibers, leading to increased compliance of the overall mesh. This allows a biomechanical stimulation of the tissue that will enable it to regenerate and remodel into a load-bearing tissue, e.g. aponeurotic structures, tendons or ligaments, which gradually will take over the load carried by the mesh implant during the time period of resorption.

The materials used to make the fibers used in the different embodiments of the present invention can be any resorbable polymer, copolymer, polymer blend or polymer composite or other suitable material, or can be combined assorted resorbable polymer parts, as long as the materials have suitable predetermined times of substantial degradation and elasticity, so that when the materials are combined, the inventive mesh implant imitates the ideal (for the particular tissue) relative distension versus time situation of a resorbable mesh implant used to temporarily support soft tissue defects during reconstruction, as described above. Non-limiting examples of such synthetic resorbable polymers are made from the monomers glycolide, lactide and all stereoisomers thereof, trimethylene carbonate, e-caprolactone, dioxanone or dioxepanone, or various combinations thereof. Depending on the desired mechanical properties and the choice of manufacturing method, several of the homopolymers or copolymers containing two or more of the above-mentioned monomers can be used to manufacture the mesh structure. Yet other examples of synthetic resorbable polymers that can be utilized are various aliphatic polyurethanes, such as polyureaurethanes, polyesterurethanes and polycarbonateurethanes, and also materials such as polyphosphazenes or polyorthoesters.

The type of knitting technique used to create the mesh implant of the present invention can be any type of knitting techniques, keeping in mind that the knit is constructed such that the overall relative distension of the inventive mesh implant is stepwise increased at the times of degradation of each set of fibers. It is preferable that the mesh implant is knitted using a technique that produces a mesh that is resistant to runs, such as a warp-knit procedure, to prevent tearing of the mesh during insertion or during the overall time of degradation of the mesh implant in the body.

The last substantially degraded material of the inventive mesh implant, preferably has a knitted structure with an aperture size preferably in the range of 0.1-4.0 mm, more preferred 0.2-2.0 mm, in order to minimize the mass of the mesh implant as well as maximizing the tissue supporting effect of said last substantially degraded material.

It will be understood that the invention is not restricted to the above described exemplifying embodiments thereof and that many modifications are conceivable. The changes in relative distension of the inventive mesh implant are further described in the following non-restrictive example.

Example 1

The overall distension of the inventive mesh implant at 16 N/cm (see K. Junge et al.: Elasticity of the anterior abdominal wall and impact for reparation of incisional hernias using mesh implants. Hernia 2001, no. 5, p. 113-118) for the ball burst testing apparatus was determined using the ASTM D3787-01 guideline for the fixture geometry (25.4 mm polished steel ball, 44.45 mm diameter inside opening). Two different meshes, knitted together in two different interlocking patterns, diamond pattern and full-tricot, were tested. Both meshes were composed of the same two types of fibers. The fast degrading fiber (40% by weight) was a tri-axial copolymer having a soft core and crystalline arms composed of 86% glycolide, the rest being trimethylenecarbonate and lactide. The slow degrading fiber (60% by weight) was a linear copolymer having a soft core and crystalline arms composed of 91.5% lactide, the rest being trimethylene carbonate. The area weight of each mesh was approximately 135 g/m$^2$.

Samples of the mesh were immersed in phosphate buffer (pH 7.4) at 37 degrees Celsius. The overall distension of the mesh was determined at different time points. The mesh was clamped in the fixture without any applied tension and the ball was positioned in the center of the 44.45 mm diameter opening. The ball was then brought down to a position on the mesh such that a 0.1 N force was applied. The test was initiated and the ball traveled at 2.54 cm/min until failure. For each test three pieces of data were recorded:
1) Maximum load obtained during the test (N)
2) The extension at the maximum load (mm)
3) The extension at 71 N load (mm)

Figure 4:
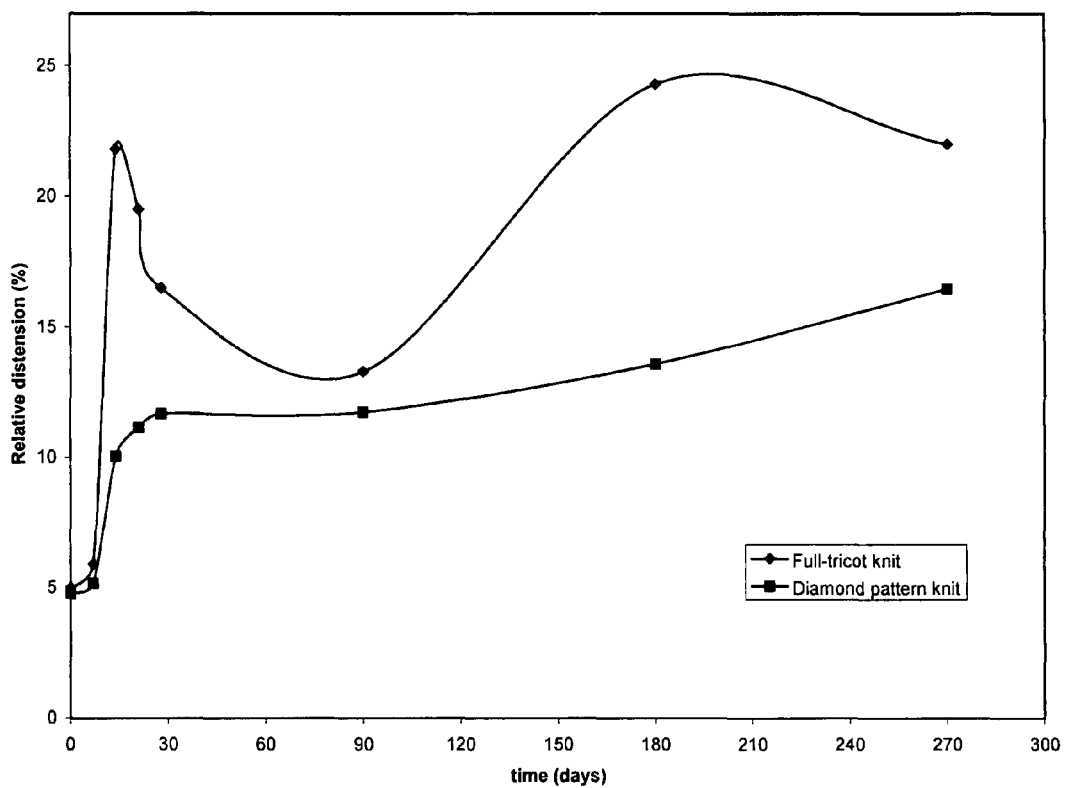
FIG. 4 shows the relative distension of the two mesh implants described in Example 1 as a function of time.

The value of 71 N is derived from the diameter of the opening (4.445 cm×16 N/cm=71 N). The extension at 71 N was used to determine the relative distension at 16 N/cm. The results are presented in FIG. 4. These results show that as the mesh decomposes over time the relative distension increases as the first material is degraded.

Although the present invention has been described with reference to specific embodiments, also illustrated by the drawings, it will be apparent for those skilled in the art that many variations and modifications can be done within the scope of the invention as described in the specification and defined with reference to the claims below. The mesh implant of the present invention has been described in the context of repair of the abdominal wall. However, it should be noted that the mesh implant can also be used as tissue support in other types of surgical procedures, such as wound healing of internal organs, muscles, tendons or other tissues. In addition, the mesh implant can be produced into other shapes than a flat mesh, such as e.g. a pouch or a pocket to support an internal organ or other structure.

The invention claimed is:

1. A resorbable polymeric mesh implant for use in reconstruction of soft tissue defects, comprising:
a first arrangement of resorbable material comprising fibers; and
a second arrangement of resorbable material comprising fibers, the second arrangement of resorbable material being substantially degradable at a later point in time than the first arrangement of resorbable material,
wherein the first arrangement of resorbable material is in contact with the second arrangement of resorbable material such that the first arrangement of resorbable material locks movement of the second arrangement of resorbable material by traversing apertures of the second arrangement of resorbable material to maintain relative distension of the mesh implant substantially constant following a time of implantation and until the first arrangement of resorbable material is substantially degraded, such that the mesh implant has a first substantially constant relative distension before the first arrangement is substantially degraded, and
wherein after the first arrangement of resorbable material is substantially degraded, the relative distension of the mesh implant substantially increases,
wherein the first arrangement of resorbable material and the second arrangement of resorbable material have different patterns,
wherein the second arrangement is a fabric having a structural integrity without a presence of the first arrangement, such that the mesh implant has a second relative distension after the first arrangement has substantially degraded, wherein the second relative distension is higher than the first relative distension.

2. A resorbable polymeric mesh implant for use in reconstruction of soft tissue defects, wherein the mesh implant comprises:
a first set of resorbable polymeric fibers, and
a second set of resorbable polymeric fibers,
wherein the fibers are knitted together,
wherein filaments of said first set of fibers are interlaced into filaments of the second set of fibers and at least partly traverse a knit pattern of the second set of fibers such that the filaments of the first set of fibers lock the movement of the part of the mesh implant formed by the second set of fibers, and
wherein the relative distension of the mesh implant is substantially constant following the time of implantation and until said first set of fibers is substantially degraded, such that the mesh implant has a first substantially constant relative distension before the first set of fibers is substantially degraded, and
wherein the second set of fibers are substantially degraded at a later point in time than the first set of fibers,
wherein the first set of resorbable polymeric fibers and the second set of resorbable polymeric fibers have different patterns,
wherein the second set of resorbable polymeric fibers is a fabric having a structural integrity without a presence of the first set of resorbable polymeric fibers, such that the mesh implant has a second relative distension after the first set of fibers has substantially degraded, wherein the second relative distension is higher than the first relative distension.

3. The resorbable polymeric mesh implant according to claim 2, wherein the mesh implant comprises a third set of fibers that is substantially degraded at a later point in time than the second set of fibers and the relative distension of the mesh implant is substantially changed after the second set of fibers is substantially degraded.

4. The resorbable polymeric mesh implant according to claim 2, wherein the different sets of fibers are made of different materials with different resorption times relative to the time of implantation.

5. The resorbable polymeric mesh implant according to claim 2, wherein the first set of fibers is substantially degraded at a point in time within the time range of 2-40 days following implantation.

6. The resorbable polymeric mesh implant according to claim 2, wherein the last substantially degraded set of fibers is substantially degraded at a point in time within the time range of 3-18 months following implantation.

7. The resorbable polymeric mesh implant according to claim 2, wherein the relative distension of the mesh implant following the time of implantation and until said first set of fibers is substantially degraded is within the range of 0-10%.

8. The resorbable polymeric mesh implant according to claim 2, wherein the relative distension of the mesh implant following the time of substantial degradation of the first set of fibers is above 10%.

9. The resorbable polymeric mesh implant according to claim 2, wherein the polymeric mesh implant is a hernia mesh implant.

10. The resorbable polymeric mesh implant according to claim 2, wherein the mesh implant stretches more in one direction along the plane of the mesh implant than in another direction along the plane of the mesh implant.

11. The resorbable polymeric mesh implant according to claim 2, wherein the polymeric mesh implant is formed into a three-dimensional shape to support an internal body structure.

12. The resorbable polymeric mesh implant according to claim 2, wherein the first set of fibers and/or further sets of fibers has or is incorporated into a knitted structure with an aperture size in the range of 0.1-4.0 mm.

13. The resorbable polymeric mesh implant according to claim 2, wherein the mesh implant is knitted using a technique that produces a mesh that is resistant to runs.

14. The method to repair a soft tissue defect, wherein a resorbable polymeric mesh implant according to claim 1 is used.

15. The resorbable polymeric mesh implant according to claim 1, wherein the polymeric mesh implant is a hernia mesh implant.

16. The resorbable polymeric mesh implant according to claim 1, wherein the arrangements are made of different materials with different resorption times relative to the time of implantation.

17. The resorbable polymeric mesh implant according to claim 1, wherein the mesh implant is fully resorbable.

18. The resorbable polymeric mesh implant according to claim 2, wherein the mesh implant is fully resorbable.

* * * * *